United States Patent [19]
Xiao et al.

[11] Patent Number: 6,130,078
[45] Date of Patent: Oct. 10, 2000

[54] **METHOD FOR CLONING THE NSPHI RESTRICTION-MODIFICATION SYSTEM IN *E. COLI* AND PRODUCING THE RECOMBINANT NSPHI RESTRICTION ENDONUCLEASE**

[75] Inventors: Jian-ping Xiao, Wenham; Shuang-yong Xu, Lexington, both of Mass.

[73] Assignee: New England Biolabs, Inc., Beverly, Mass.

[21] Appl. No.: 09/193,191

[22] Filed: Nov. 17, 1998

[51] Int. Cl.[7] .............................. C12N 9/22; C12N 15/55
[52] U.S. Cl. .................. 435/199; 435/320.1; 435/252.3; 536/23.2
[58] Field of Search ................ 435/199, 320.1, 435/252.3; 536/23.2

[56] References Cited

U.S. PATENT DOCUMENTS 5,200,333  4/1993  Wilson .................................. 435/172.3
5,498,535  3/1996  Fomenkov et al. ................... 435/172.3

OTHER PUBLICATIONS

Roberts et al, Nucl. Acids Res. 26:338–350 (1998).
Kosykh et al., Mol. Gen Genet. 178:717–719 (1980).
Mann et al., Gene 3:97–112 (1978).
Walder et al., Proc. Nat. Acad. Sci. 78:1503–1507 (1981).
Bouqueleret et al., Nucl. Acids. Res. 12:3659–3676 (1984).
Gingeras et al., Proc. Natl. Acad. Sci. USA 80:402–406 (1983).
Theriault et al., Gene 19:355–359 (1982).
Blumenthal et al., J. Bacteriol. 164:501–509 (1985).
Wayne et al., Gene 195:321–328 (1997).
Kiss et al., Nucl. Acids. Res. 13:6403–6421 (1985).
Szomolanyi et al., Gene 10:219–225 (1980).
Janulaitis et al., Gene 20:197–204 (1982).
Kiss et al., Gene 21:111–119 (1983).
Walder et al., J. Biol. Chem. 258:1235–1241 (1983).
Fomenkov et al., Nucl. Acids Res. 22:2399–2403 (1994).
Xu, S–Y., et al. (1998) Mol. Gen. Genet. 260, 226–231.
Duyvesteyn, M.G.C., et al. (1983) Arch Microbiol. 134, 276–281.
Lunnen, K.D., et al. (1988) Gene 74, 25–32.

*Primary Examiner*—Charles L. Patterson, Jr.
*Attorney, Agent, or Firm*—Gregory D. Williams

[57] ABSTRACT

The present invention relates to recombinant DNA molecules encoding NspHI restriction endonuclease and methylase and to method to use premodified *E. coli* K strain RR1 (λDE3) for overexpression of NspHI restriction endonuclease.

6 Claims, 3 Drawing Sheets

DILUTION  $10^{-1}$  $10^{-2}$  $10^{-3}$  $10^{-4}$  $10^{-5}$

FIG. 2

```
    ATGCAAAGCACACAACTTTCTTTTTTTCCTGATGAAGATGAGAATAAGTCTACTAAAAAG
1   ------------+---------+---------+---------+---------+---------+  60
     M  Q  S  T  Q  L  S  F  F  P  D  E  D  E  N  K  S  T  K  K
    CAAAAAAAAACCAAAGTTAGGGCGTTATGAACGGATAAAACGCGAACTAGAAAACAATGAC
61  ------------+---------+---------+---------+---------+---------+ 120
     Q  K  K  P  K  L  G  R  Y  E  R  I  K  R  E  L  E  N  N  D
    ATAGATCCTTACAAGAAATTTATTGATGTCGATACCCCACTAATAGCAGCATCTCAATAT
121 ------------+---------+---------+---------+---------+---------+ 180
     I  D  P  Y  K  K  F  I  D  V  D  T  P  L  I  A  A  S  Q  Y
    AATTTTGTGGATcTATTTTGTGGAGCAGGAGGAATTACTCAAGGACTAATACAGGCTGGA
181 ------------+---------+---------+---------+---------+---------+ 240
     N  F  V  D  L  F  C  G  A  G  G  I  T  Q  G  L  I  Q  A  G
    TTCCAAGCATTAGCAAGTGTAGAAACTAGTTCAATTGCTTcTGCTACACATCAAAGAAAT
241 ------------+---------+---------+---------+---------+---------+ 300
     F  Q  A  L  A  S  V  E  T  S  S  I  A  S  A  T  H  Q  R  N
    TTTCCTCATTGTCATCATTTTTGTGGAGATATTGAACAATTTTCCCCAAAGATTTGGTTG
301 ------------+---------+---------+---------+---------+---------+ 360
     F  P  H  C  H  H  F  C  G  D  I  E  Q  F  S  P  K  I  W  L
    AAACAAATCGGATCTCCTGAAGTAAATCTTGTTGTTGGTGGGCCTCCTTGTCAAGGATTC
361 ------------+---------+---------+---------+---------+---------+ 420
     K  Q  I  G  S  P  E  V  N  L  V  V  G  G  P  P  C  Q  G  F
    TCAGTTGCTGGTAAACGCGATCCCAAAGACCCACGGAATCGCCTCTTTTATGAATTTGTG
421 ------------+---------+---------+---------+---------+---------+ 480
     S  V  A  G  K  R  D  P  K  D  P  R  N  R  L  F  Y  E  F  V
    CGGGTGGTATCAGAGATACGCCCTTGGTATGTAGTGATGGAAAACGTACCAGGAATACTC
481 ------------+---------+---------+---------+---------+---------+ 540
     R  V  V  S  E  I  R  P  W  Y  V  V  M  E  N  V  P  G  I  L
    ACTATCCAAAATGGAAATGTCAAGCAAGCAATTATTGAGGCTTTTGAGTCTATTGGTTAT
541 ------------+---------+---------+---------+---------+---------+ 600
     T  I  Q  N  G  N  V  K  Q  A  I  I  E  A  F  E  S  I  G  Y
    CCCAATATATCTGTAGCAATTTTAGAATCTGCTGATTATGGAATACCACAAATTAGACCA
601 ------------+---------+---------+---------+---------+---------+ 660
     P  N  I  S  V  A  I  L  E  S  A  D  Y  G  I  P  Q  I  R  P
    AGAGCAATTTTTATTGCTAATAGATTTGGAATGCCAAACCCTTATCCCAAGGCTCAGTTA
661 ------------+---------+---------+---------+---------+---------+ 720
     R  A  I  F  I  A  N  R  F  G  M  P  N  P  Y  P  K  A  Q  L
    TCACCTGAAAAATATAAACCTATTGAATCAGCTATTTCTGACTTACCAGAATATACTCCG
721 ------------+---------+---------+---------+---------+---------+ 780
     S  P  E  K  Y  K  P  I  E  S  A  I  S  D  L  P  E  Y  T  P
    ATACCAGAAATTAATCATCAATGGACTAGACATTCACCAGAGTATATGGAGCGAATTGCA
781 ------------+---------+---------+---------+---------+---------+ 840
     I  P  E  I  N  H  Q  W  T  R  H  S  P  E  Y  M  E  R  I  A
    AAAGTACCCCCTGGCGGTTCTTTGTATCAAAAATATGTTGATGCCTTTAAGCGTCAATAT
841 ------------+---------+---------+---------+---------+---------+ 900
     K  V  P  P  G  G  S  L  Y  Q  K  Y  V  D  A  F  K  R  Q  Y
    CCTGGTAAGCCAAGCATGACTGTTAAAGAAAATCATGGCGGTACTCATATTCACCCATAT
901 ------------+---------+---------+---------+---------+---------+ 960
     P  G  K  P  S  M  T  V  K  E  N  H  G  G  T  H  I  H  P  Y
    TTAAATAGGGTAATTTCAGCTCGTGAGATGGCAAGATTACAAACATTTCCTGATTCATTC
961 ------------+---------+---------+---------+---------+---------+1020
     L  N  R  V  I  S  A  R  E  M  A  R  L  Q  T  F  P  D  S  F
    ATTTTTGAAGGGACAAT GCAATGTGGCAAATTGGTAATGCTGTACCGCCACCGCCACGT
1021------------+---------+---------+---------+---------+---------+1080
     I  F  E  G  T  M  K  K  A  M  W  Q  I  G  N  A  V  P  P  R
    TTAGCAGAATGTATCGGCTATGCACTAATACCTTATTTAAATAAGATTGCGCTTAATACT
1081------------+---------+---------+---------+---------+---------+1140
     L  A  E  C  I  G  Y  A  L  I  P  Y  L  N  K  I  A  L  N  T
    AAGAATAAAGTTGATGTTACTTGTATTGATCAGACTGAGTTAGTGTTTGATTAA
1141------------+---------+---------+---------+---------+----         1194
```

FIG. 3

```
     GTGAATGAAGAACAAAATCTAGTAGAGATAATTCAGCGCCAGTTCAGACAAAACTCAACT
  1  ------------+---------+---------+---------+---------+---------+  60
     M  N  E  E  Q  N  L  V  E  I  I  Q  R  Q  F  R  Q  N  S  T
     CAACTACAAGTCTTTAACCTCTTATCAGATGAAAAATGGCATTGTAGGGAATGTG1UGGT
 61  ------------+---------+---------+---------+---------+---------+  120
     Q  L  Q  V  F  N  L  L  S  D  E  K  W  H  C  R  E  C  E  G
     AAGAAAATAGGCTCAAATCAGTACGCTGGTGGTGGAGGTATTCAGGGGTTACAACGTGGG
121  ------------+---------+---------+---------+---------+---------+  180
     K  K  I  G  S  N  Q  Y  A  G  G  G  G  I  Q  G  L  Q  R  G
     ACAAGGAGTCGTCCAGGTCTTGTAATTGAAACGACCAAGAATTACTGTCCAACTTGTCAA
181  ------------+---------+---------+---------+---------+---------+  240
     T  R  S  R  P  G  L  V  I  E  T  T  K  N  Y  C  P  T  C  Q
     CAAGTACGCTTAGGAGATCAATGGACAGGAGAGATTAAATCAGCTAATTCCGCATCAAAT
241  ------------+---------+---------+---------+---------+---------+  300
     Q  V  R  L  G  D  Q  W  T  G  E  I  K  S  A  N  S  A  S  N
     ATACCAGCGTCTTTAGTTGAGAGAATTTTTACAAGTTATTCCTATACAGATGTAATAGAA
301  ------------+---------+---------+---------+---------+---------+  360
     I  P  A  S  L  V  E  R  I  L  Q  V  Y  S  Y  T  D  V  I  E
     CAAAGACAGAGAGAAAAACATGAATTGGTAATTGATCATCGATTCCCGATGGAACGTTGG
361  ------------+---------+---------+---------+---------+---------+  420
     Q  R  Q  R  E  K  H  E  L  V  I  D  H  R  F  P  M  E  R  W
     GGAGCTAGTGAGCCTCCACACTTAACTTCTTCTATGAGTGATGAAATTAAGCAAAAGTTT
421  ------------+---------+---------+---------+---------+---------+  480
     G  A  S  E  P  P  H  L  T  S  M  S  D  D  E  I  K  Q  K  F
     CAATTGTTAAAAAAAGACGCATCAGGTAATCACAATCTTTTAAAATCGAGAAGTTGTGAG
482  ------------+---------+---------+---------+---------+---------+  540
     Q  L  L  K  K  D  A  S  G  N  H  N  L  L  K  S  R  S  C  E
     CGCTGTATCAAAACTGGTAAAAGAGGTACACCTATAGGCATCCATTTTTGGTATCAAGGT
541  ------------+---------+---------+---------+---------+---------+  600
     R  C  I  K  T  G  K  R  G  T  P  I  G  I  H  F  W  Y  Q  G
     GGAGAAGATTGGCCTTCTCCACATCAACGTGGTGCTGAAGCAGAAGAAGGCTGTGTTGGA
601  ------------+---------+---------+---------+---------+---------+  660
     G  E  D  W  P  S  P  H  Q  R  G  A  E  A  E  E  G  C  V  G
     TGTGGTTGGTATAATTTTGAAGTATGGCGTAACGCTATTAATCAAACACTAACTCAGTCT
661  ------------+---------+---------+---------+---------+---------+  720
     C  G  W  Y  N  F  E  V  W  R  N  A  I  N  Q  T  L  T  Q  S
     GATCAATACAAGTAA
721  ------------+------  735
     D  Q  Y  K  *
```

METHOD FOR CLONING THE NSPHI RESTRICTION-MODIFICATION SYSTEM IN E. COLI AND PRODUCING THE RECOMBINANT NSPHI RESTRICTION ENDONUCLEASE

BACKGROUND OF THE INVENTION

The present invention relates to recombinant DNA which encodes the NspHI restriction endonuclease as well as NspHI methylase, the production of NspHI restriction endonuclease from the recombinant DNA, and purification of the recombinant NspHI from *E. coli* cell extract.

Type II restriction endonucleases are a class of enzymes that occur naturally in bacteria. When they are purified away from other bacterial components, restriction endonucleases can be used in the laboratory to cleave DNA molecules into small fragments for generating recombinant DNA molecules.

Restriction endonucleases act by recognizing and binding to particular sequences of nucleotides along the DNA molecule. Once bound, they cleave the molecule within, to one side of, or to both sides of the recognition sequence. Different restriction endonucleases have affinity for different recognition sequences. Over two hundred and twenty restriction endonucleases with unique specificities have been identified among the many hundreds of bacterial species that have been examined to date (Roberts and Macelis, Nucl. Acids Res. 26:338–350, (1998)).

Restriction endonucleases typically are named according to the bacteria from which they are derived. Thus, the species *Deinococcus radiophilus* for example, produces three different restriction endonucleases, named DraI, DraII and DraIII. These enzymes recognize named DraI, DraII and DraIII. These enzymes recognize and cleave the sequences 5'TTTAAA3', 5'PuGGNCCPy3' and 5'CACNNNGTG3' respectively. *Escherichia coli* RY13, on the other hand, produces only one enzyme, EcoRI, which recognizes the sequence 5'GAATTC3'.

A second component of bacterial restriction-modification (R-M) systems are the methylases. These enzymes provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is fully modified and it is therefore completely insensitive to the presence of the endogenous restriction endonuclease. It is only unmodified, and therefore identifiably foreign DNA, that is sensitive to restriction endonuclease recognition and cleavage.

With the advent of recombinant DNA technology, it is now possible to clone genes and overproduce the enzymes in large quantities. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are cloned by a number of methods. The first cloned systems used bacteriophage infection as a means of selecting restriction endonuclease clones (EcoRII: Kosykh et al., Mol. Gen. Genet. 178:717–719, (1980); HhaII: Mann et al., Gene 3:97–112, (1978); PstI: Walder et al., Proc. Nat. Acad. Sci. 78:1503–1507, (1981)). Since the presence of restriction-modification systems in bacteria enable them to resist infection by bacteriophages, cells that carry cloned restriction-modification genes can, in principle, be selectively isolated as survivors from libraries that have been exposed to bacteriophages. However, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., Nucl. Acids. Res. 12:3659–3676, (1984); PaeR7: Gingeras and Brooks, Proc. Natl. Acad. Sci. USA 80:402–406, (1983); Theriault and Roy, Gene 19:355–359 (1982); PvuII: Blumenthal et al., J. Bacteriol. 164:501–509, (1985); Tsp45I: Wayne and Xu, Gene 195:321–328 (1997)).

A third approach, the selection for an active methylase gene has been used to clone a large number of R-M systems (U.S. Pat. No. 5,200,333 and BsuRI: Kiss et al., Nucl. Acids. Res. 13:6403–6421, (1985)). Since R-M genes are organized in close proximity to each other, both genes can often be cloned simultaneously. This selection does not always yield a complete restriction system however, but instead yields only the methylase gene (BspRI: Szomolanyi et al., Gene 10:219–225, (1980); BcnI: Janulaitis et al., Gene 20:197–204 (1982); BsuRI: Kiss and Baldauf, Gene 21:111–119, (1983); and MspI: Walder et al., J. Biol. Chem. 258:1235–1241, (1983)).

A more recent method, the "endo-blue method", has been described for direct cloning of restriction endonuclease genes in *E. coli* based on the indicator strain of *E. coli* containing the dinD::lacZ fusion (Fomenkov et al., U.S. Pat. No. 5,498,535; Fomenkov et al., Nucl. Acids Res. 22:2399–2403, (1994)). This method utilizes the *E. coli* SOS response following DNA damages caused by restriction endonucleases or non-specific nucleases. A number of thermostable nuclease genes (TaqI, Tth111I, BsoBI, Tf nuclease) have been cloned by this method (U.S. Pat. No. 5,498,535).

Because purified restriction endonucleases are useful tools for creating recombinant molecules in the laboratory, there is a commercial incentive to obtain bacterial strains through recombinant DNA techniques that produce these enzymes in large quantities. Such overexpression strains would also simplify the task of restriction enzyme purification.

SUMMARY OF THE INVENTION

In accordance with the present invention there is provided a clone containing the gene coding for NspHI restriction endonuclease derived from Nostoc species (ATCC 29106). The present invention also relates to clones which express recombinant NspHI restriction endonuclease and NspHI methylase and to methods for cleaves between the fifth and sixth bases on both strands leaving a 4 base 3' extension. The native Nostoc species (ATCC 29106) produces two restriction endonucleases NspHI and NspHII. By cloning the NspHI R-M system in *E. coli*, one can avoid the possible contamination of NspHII.

The cloning of DNA encoding the NspHI modification methylase and a portion of the nspIR was achieved by methylase selection and DNA sequencing of nspIM gene and the adjacent DNA. The rest of the nspIR gene was isolated by inverse PCR of the adjacent DNA to the partial open reading frame (ORF). To premodify *E. coli* host DNA, the nspHIM gene was amplified by PCR and cloned in a compatible plasmid pACYC184 to generate pACYC- NspHIM. The nspHIR gene was amplified by PCR and cloned in a T7 expression vector pET21at. However, the expression strain (*E. coli* B strain), ER2504 [pACYC-NspHIM, pET21at-NspHIR], was not stable, probably due to the constitutive expression of NspHI and methylation-dependent restriction. To construct a stable overexpression clone, *E. coli* K strain RR1($\lambda$DE3) was used as the expression host. In addition, a third compatible plasmid pCEF8 carrying the T7 lysozyme gene was introduced into the host. This overexpression strain, RR1($\lambda$DE3) [pACYC-NspHIM, pET21at-NspHIR, pCEF8] produced approximately 186,000 units of recombinant NspHI per gram of wet *E. coli* cells.

BRIEF DESCRIPTION OF THE DRAWINGS

FIG. 2 shows the DNA sequence (SEQ ID NO:1) of nspHIM gene and its predicted amino acid sequence (SEQ ID NO:2).

FIG. 3 shows the DNA sequence (SEQ ID NO:3) of nspHIR gene and its predicted amino acid sequence (SEQ ID NO:4).

DETAILED DESCRIPTION OF THE INVENTION

The present invention relates to clones of the NspHI restriction and modification genes, as well to the recombinant NspHI restriction endonuclease produced from such clones.

The method described herein by which the NspHI restriction gene and methylase gene are preferably cloned and expressed includes the following steps:

1. The DNA of Nostoc species (ATCC No. 29106) is purified. This strain is available from American Tissue Type Culture Collection.

2. The DNA is digested partially with restriction endonucleases such as ApoI (5' RAATTY 3') and Tsp509I (5'AATT 3') or any isoschizomers. The ApoI or Tsp509I partially digested DNA is ligated to EcoRI digested and CIP treated RRS derivative (this modified vector contains two NspHI sites).

3. The ligated DNA mixture is heated at 65° C. for 30 min to inactivate T4 DNA ligase and then dialysed in 2 L of distilled H$_2$O by drop dialysis. It is then used to transform an appropriate host such as *E. coli* RR1 cells by electroporation. The DNA/cell mixture is plated on ampicillin plates for transformed cells. After incubation, the transformed colonies are collected together into a single culture, the primary cell library. The recombinant plasmids are purified in toto from the primary cell library to make a primary plasmid library.

4. The ApoI and Tsp509I partial DNA libraries are then digested in vitro with the NspI restriction endonuclease (NspI and NspHI are isoschizomers). NspI restriction digestion causes the selective destruction of unmodified, non-methylase-containing, clones, resulting in an increase in the relative frequency of NspHI methylase-carrying clones.

5. The digested plasmid library DNA is transformed back into an *E. coli* host such as RR1, and transformed colonies are again obtained by plating on Amp plates. The colonies are picked and their DNA is analyzed for the presence of the NspHI modification in the following manner: The plasmid DNA is purified and incubated in vitro with NspI restriction endonuclease to determine whether it is resistant to digestion by NspI. The DNA of clones that carry the NspHI methylase gene should be fully or partially modified and resistant to NspI digestion. Twelve plasmids were found to be resistant to NspI digestion in the ApoI partial DNA library. resistant to NspI digestion in the ApoI partial DNA library.

6. Once the resistant clone is identified, the insert DNA is mapped by restriction mapping. Deletion clones and subclones are constructed in pUC19 and sequenced using pUC19 universal primers and custom-made primers. Plasmid DNA is sequenced by the dideoxy termination method.

Figure 1:
FIG. 1 illustrates the gene organization of NspHI restriction-modification system.

7. After the entire insert is sequenced, the DNA sequence is translated into amino acid sequences. Two open reading frames and one partial ORF are found. One ORF contains ten conserved sequence motifs of C5 methylases and is assigned as nspHIM gene (FIGS. 1 and 2). The second ORF upstream of the nspHIM gene encodes a protein that has high homology to amino peptidases. The third ORF is a partial reading frame missing the start codon. Inverse PCR primers are made based on the known DNA sequence of this partial ORF. The adjacent DNA is amplified by inverse PCR. Inverse PCR products are sequenced and the start codon for the nspHIR gene is identified. The nspHIR gene is 732 bp, running toward the nspHIM gene (FIGS. 1 and 3).

8. The nspHIM gene (1191 bp) is amplified by PCR and cloned into BamHI-digested and CIP treated pACYC184 vector. The premodified expression host is an *E. coli* B strain ER2504 [pACYC-NspHIM]. The nspHIR endonuclease gene is amplified from Nostoc species genomic DNA using Vent® DNA polymerase and two primers in PCR and ligated into a BamHI digested and CIP treated pET21at expression vector. The expression strain is ER2504 [pACYC-NspHIM, pET21at-NspHIR]. This strain, however, is not stable in 1 L cell culture.

Figure 4:
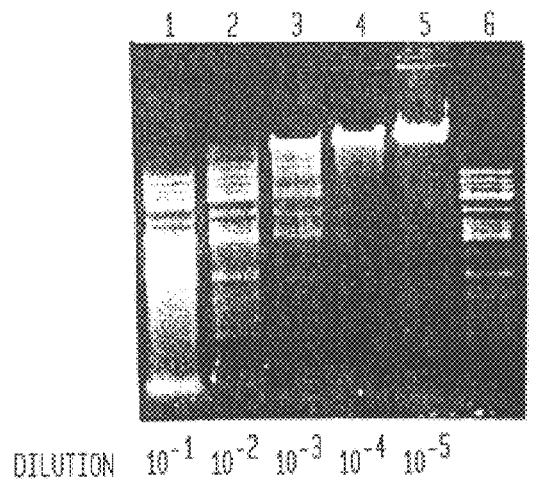
FIG. 4 illustrates the NspHI restriction enzyme activity from *E. coli* cell extract. Lanes 1, 2, 3, 4, and 5, digestion of $\lambda$ DNA with $10^{-1}$, $10^{-2}$, $10^{-3}$, $10^{-4}$, and $10^{-5}$ -fold dilution of cell extract, respectively; lane 6, a positive control, NspI digestion of $\lambda$ DNA.

9. To construct a stable expression strain, an *E.coli* K strain RR1($\lambda$DE3) is used as the expression host. In addition, a third plasmid, pCEF8 (the T7 lysozyme gene is inserted in the pSYX20 carrying pSC101 origin, William E. Jack, New England Biolabs, Inc., Beverly, Mass.) is introduced into the expression strain. The final NspHI expression strain is RR1 ($\lambda$DE3) [PACYC-NspHIM, pET21at-NspHIR, pCEF8]. Cell extracts are prepared from the IPTG-induced cells and assayed for NspHI endonuclease activity on $\lambda$ DNA. The overexpression strain produced about 186,000 units of NspHI restriction endonuclease activity per gram of wet cells (FIG. 4).

The present invention is further illustrated by the following Example. This Example is provided to aid in the understanding of the invention and is not construed as a limitation thereof.

The references cited above and below are herein incorporated by reference.

EXAMPLE 1

Cloning and Expression of NspHI Restriction-Modification System in *E. coli*

1. Construction of an ApoI Partial Genomic DNA Library

Ten $\mu$g of Nostoc sp. (ATCC number 29106) genomic DNA was digested with 2, 1, 0.5, and 0.25 units of ApoI at 50° C. for 30 min. Nostoc sp. genomic DNA was also partially digested with Tsp509I at 65° C. 0.25 units of digestion gave rise to the desired partial digestion. The partially digested DNA in the range of 1.5–6 kb was gel purified in a 1% low melting agarose gel. The purified genomic DNA was digested with $\beta$-agarase and precipitated by ethanol. The genomic DNA was then ligated into EcoRI cut and CIP treated vector pRRS at 16° C. overnight. (The modified pRRS vector contains two NspHI sites). The ligated DNA was transformed into RR1 electro-competent cells by electroporation. About $10^5$ Ap$^R$ transformants were obtained. All the transformants were pooled and amplified in 2 L overnight cell culture. Plasmids were prepared from the overnight cells to form the primary plasmid library.

2. Challenge the ApoI Partial DNA Library by NspI Digestion and Cloning of the NspHI Methylase Gene (nspHIM)

About 1 μg of the plasmid library DNA was digested with 30 units of NspI at 37° C. for 4 hours. DNA was precipitated by ethanol and the resuspended DNA was digested with same amount of NspI for another 2 hours. The digested DNA was used to retransform RR1 competent cells. Transformants were plated on Amp plates. Plasmid DNA was isolated from 1.5 ml cell culture of 30 transformants by Qiagen (Studio City, Calif.) mini spin columns. The DNA was digested with NspI to detect any resistance to NspI digestion. Eleven plasmid isolates (#2, #3, #4, #9 #10, #11, #12, #13, #14, #20, #25, and #26) displayed resistance to NspI digestion. Restriction digestion of #3 clone plasmid DNA with PvuII indicated that it contains an insert of approximately 6 kb.

The #2 plasmid DNA was digested with HindIII and XbaI, respectively. One HindIII fragment and two XbaI fragments were gel purified and subcloned into pUC19. The inserts in the subclones were sequenced using pUC19 forward and reverse primers. When the sequences were compared to the known methylase genes in GenBank using blastx, no homology was found. In order to locate the methylase in this large insert, the following deletions were made: Δ(EcoO109-EcoNI), Δ(EcoO109-EcoRV), XbaI$^Δ$, Δ(EcoRV-BamHI), HindIII$^Δ$, Δ(AflIII-BamHI), Δ(AflIII-EcoO109), Δ(EcoNI-BamHI). The deletion clone Δ(EcoNI-BamHI was sequenced using both forward and reverse primers and three other synthesized primers according to the known sequence in this clone. The entire NspHI methylase gene (nspHIM) of 1191 bp was found (FIGS. 1 and 2).

DNA sequencing upstream and downstream of the nspHIM gene revealed one ORF and one partial ORF. The gene upstream codes for a protein that has high homology to amino peptidases and the partial ORF downstream has no homology to any genes/proteins in GenBank. Since restriction-modification genes are located in adjacent to each other, it was concluded that the partial ORF is most likely the nspHIR gene. Efforts were made to clone the missing portion of the partial ORF.

3. Cloning of NspHI Restriction Endonuclease Gene (nspHIR)

Inverse PCR was carried out to clone the genomic DNA downstream of the NspHI methylase gene. A set of inverse PCR primers was made based on the end of the known sequence:

```
5' GTCTTTGTTCTATTACATCTGTATAGG 3' (159-67)   (SEQ ID NO:5)

5' CATGAATTGGTAATTGATCATCGATTC 3' (159-68R)  (SEQ ID NO:6)
```

Genomic DNA was digested with AluI, AseI, BfaI, DraI, Eco47III, HaeII, HhaI, HinPII, MfeI, MseI, and RsaI respectively. The PCR was performed at 94° C. 1', 55° C. 1', 72° 2', for 30 cycles. Products were obtained from the HinP1I and MfeI cut and self ligated templates.

The HinP1I DNA fragment was gel purified and cloned into pUC19. Plasmid DNA was made from the transformants and sequenced using primers 159–167, 159–168R. The newly derived sequence was 340 bp. To clone the rest part of the restriction endonuclease, a second set of primers were made based on the newly derived 340 bp sequence:

```
5' AGGTTAAAGACTTGTAGTTGAGTTGAG 3' (160-79)   (SEQ ID NO:7)

5' AAAATGGCATTGTAGGGAATGTGAAGG 3' (160-80)   (SEQ ID NO:8)
```

The genomic DNA was digested with AciI, AluI, BspDI, BstNI, DdeI, HincII, HinfI, MboI, Sau3AI, ScrFI. Inverse PCR was performed at 95° C. 1', 55° C. 1', 72° C. 2', for 30 cycles. Inverse PCR products were found in AciI, HinfI and Sau3AI digested and self-ligated templates. The AciI fragment was gel purified and cloned into pUC19 vector. The DNA was sequenced with primers 160-79 and 160-80. The nspHIR gene start codon was found in the newly extended sequence. The nspHIR gene is 732 bp, running toward the nspHIM gene (FIGS. 1 and 3).

4. Expression of nspHIM Gene in E. coli

The nspHIM gene (1191 bp) was amplified by PCR from deletion clone Δ(EcoRV-BamHI) using Vent® DNA polymerase and two primers under PCR condition of 95° C. 1' 60° C. 1' 72° C. 1.5', for 20 cycles. The two primers contains BamHI sites at the 5' ends and have the following sequence:

```
5'GCTGGATCCGGAGGTTAATTAAATGCAAAGCACACAACTTTCTTTTTTTCCT3' (161-81) (SEQ ID NO:9)

5' CTAGGATCCTTAATCAAACACTAACTCAGTCTGATCAATACA 3'          (161-96) (SEQ ID NO:10)
```

The PCR product was digested with BamHI and cloned into BamHI-digested and CIP treated pACYC184 vector. Eighteen plasmid isolates were digested with NspI and three isolates(#11, #13, #16) displayed full resistance to the NspI digestion.

5. Expression of NspHI Endonuclease Gene (nspHIR) in a T7 Expression Vector pET21at The nspHIR endonuclease gene was amplified from Nostoc species genomic DNA using Vent® DNA polymerase and two primers in PCR (95° C. 1', 60° C. 1', 72° C. 1', for 20 cycles). The PCR primers have the following sequence:

```
5'ACAGGATCCGGAGGTTAATTAAGTGAATGAAGAACAAAATCTAGTAGAGATA3',  (162-140) (SEQ ID NO:11)

5' ATTGGATCCTTACTTGTATTGATCAGACTGAGTTAGTGTTTG 3'            (162-141) (SEQ ID NO:12)
```

The PCR DNA was digested with BamHI and ligated into a BamHI digested and CIP treated pET21at expression vector. The ligated DNA was used to transform NspHI methylase modified cell ER2504 [pACYC-NspHIM]. The expression strain is ER2504 [pACYC-NspHIM, pET21at- NspHIR]. This strain, however, is not stable in 1 L cell culture. The strain lost NspHI activity in large cultures.

In order to construct a stable expression strain, an *E. coli* K strain RR1(λDE3) is used as the expression host. RR1 cells were lysogenized with λDE3 to generate RR1(λDE3). In addition, a third plasmid, pCEF8 (the T7 lysozyme gene is inserted in pSYX20 carrying pSC101 origin, William E. Jack, New England Biolabs) is introduced into the expression strain. The final NspHI expression strain is RR1(λDE3) [pACYC-NspHIM, pET21at-NspHIR, pCEF8]. Fourteen isolates were grown in LB broth containing Cam, Kan (Kanamycin) and Amp for 3 hours at 30° C. and then IPTG was added to induce the NspHI endonuclease production for 2 hours. Cell extracts were prepared from the IPTG-induced cells and assayed for NspHI endonuclease activity on lambda DNA. Eleven clones (#2–190 12) displayed NspHI activities. Clone #12 in 500 ml cell culture was induced with IPTG. The overexpression strain produced about 186,000 units of NspHI restriction endonuclease activity per gram of wet cells (FIG. 4). This expression clone is more stable in large cultures.

A sample of the NEB#1151 which contains NspHI R-M genes has been deposited under the terms and conditions of the Budapest Treaty with the American Type Culture Collection on Nov. 17, 1998 and received ATCC Accession Number 98989.

What is claimed is:

1. Isolated DNA coding for the NspHI restriction endonuclease, wherein the isolated DNA is obtainable from Nostoc species (ATCC 29106).

2. A recombinant DNA vector comprising a vector into which a DNA segment encoding the NspHI restriction endonuclease has been inserted.

3. Isolated DNA encoding the NspHI restriction endonuclease and methylase, wherein the isolated DNA is obtainable from ATCC No. 98989.

4. A cloning vector which comprises the isolated DNA of claim 3.

5. A host cell transformed by the vector of claim 2.

6. A method of producing NspHI restriction endonuclease comprising culturing a host cell transformed with the vector of claims 2 or 4 under conditions suitable for expression of said endonuclease.

* * * * *

UNITED STATES PATENT AND TRADEMARK OFFICE

CERTIFICATE OF CORRECTION

PATENT NO.:     6,130,078

DATED:          October 10, 2000

INVENTOR(S):    Jian-ping Xiao and Shuang-yong Xu

It is certified that errors appear in the above-identified patent and that said Letters Patent is hereby corrected as shown below:

Column 1, lines 33-34    delete "These enzymes recognize named DraI, DraII and DraIII."
Column 4, lines 6-7      after "DNA library." delete "resistant to NspI digestion in the ApoI partial DNA library"
Column 5, line 47        after "located" delete "in"
Column 6, line 9         replace "HinP11" with --HinP1I--
Column 6, line 15        delete "part"
Column 6, line 16        replace "were" with --was--
Column 6, line 38        replace "contains" with --contain--

Signed and Sealed this

Eighth Day of May, 2001

Attest:

NICHOLAS P. GODICI

Attesting Officer      Acting Director of the United States Patent and Trademark Office

SEQUENCE LISTING

```
<160> NUMBER OF SEQ ID NOS: 12

<210> SEQ ID NO 1
<211> LENGTH: 1194
<212> TYPE: DNA
<213> ORGANISM: Nostoc sp.
<220> FEATURE:
<221> NAME/KEY: CDS
<222> LOCATION: (1)..(1194)

<400> SEQUENCE: 1 atg caa agc aca caa ctt tct ttt ttt cct gat gaa gat gag aat aag       48
Met Gln Ser Thr Gln Leu Ser Phe Phe Pro Asp Glu Asp Glu Asn Lys
  1               5                  10                  15 tct act aaa aag caa aaa aaa cca aag tta ggg cgt tat gaa cgg ata       96
Ser Thr Lys Lys Gln Lys Lys Pro Lys Leu Gly Arg Tyr Glu Arg Ile
             20                  25                  30 aaa cgc gaa cta gaa aac aat gac ata gat cct tac aag aaa ttt att      144
Lys Arg Glu Leu Glu Asn Asn Asp Ile Asp Pro Tyr Lys Lys Phe Ile
         35                  40                  45 gat gtc gat acc cca cta ata gca gca tct caa tat aat ttt gtg gat      192
Asp Val Asp Thr Pro Leu Ile Ala Ala Ser Gln Tyr Asn Phe Val Asp
     50                  55                  60 cta ttt tgt gga gca gga gga att act caa gga cta ata cag gct gga      240
Leu Phe Cys Gly Ala Gly Gly Ile Thr Gln Gly Leu Ile Gln Ala Gly
 65                  70                  75                  80 ttc caa gca tta gca agt gta gaa act agt tca att gct tct gct aca      288
Phe Gln Ala Leu Ala Ser Val Glu Thr Ser Ser Ile Ala Ser Ala Thr
                 85                  90                  95 cat caa aga aat ttt cct cat tgt cat cat ttt tgt gga gat att gaa      336
His Gln Arg Asn Phe Pro His Cys His His Phe Cys Gly Asp Ile Glu
            100                 105                 110 caa ttt tcc cca aag att tgg ttg aaa caa atc gga tct cct gaa gta      384
Gln Phe Ser Pro Lys Ile Trp Leu Lys Gln Ile Gly Ser Pro Glu Val
        115                 120                 125 aat ctt gtt gtt ggt ggg cct cct tgt caa gga ttc tca gtt gct ggt      432
Asn Leu Val Val Gly Gly Pro Pro Cys Gln Gly Phe Ser Val Ala Gly
    130                 135                 140 aaa cgc gat ccc aaa gac cca cgg aat cgc ctc ttt tat gaa ttt gtg      480
Lys Arg Asp Pro Lys Asp Pro Arg Asn Arg Leu Phe Tyr Glu Phe Val
145                 150                 155                 160 cgg gtg gta tca gag ata cgc cct tgg tat gta gtg atg gaa aac gta      528
Arg Val Val Ser Glu Ile Arg Pro Trp Tyr Val Val Met Glu Asn Val
                165                 170                 175 cca gga ata ctc act atc caa aat gga aat gtc aag caa gca att att      576
Pro Gly Ile Leu Thr Ile Gln Asn Gly Asn Val Lys Gln Ala Ile Ile
            180                 185                 190
```

-continued

| | | |
|---|---|---|
| gag gct ttt gag tct att ggt tat ccc aat ata tct gta gca att tta<br>Glu Ala Phe Glu Ser Ile Gly Tyr Pro Asn Ile Ser Val Ala Ile Leu<br>            195                    200              205 | 624 |
| gaa tct gct gat tat gga ata cca caa att aga cca aga gca att ttt<br>Glu Ser Ala Asp Tyr Gly Ile Pro Gln Ile Arg Pro Arg Ala Ile Phe<br>210                    215                    220 | 672 |
| att gct aat aga ttt gga atg cca aac cct tat ccc aag gct cag tta<br>Ile Ala Asn Arg Phe Gly Met Pro Asn Pro Tyr Pro Lys Ala Gln Leu<br>225                    230                    235              240 | 720 |
| tca cct gaa aaa tat aaa cct att gaa tca gct att tct gac tta cca<br>Ser Pro Glu Lys Tyr Lys Pro Ile Glu Ser Ala Ile Ser Asp Leu Pro<br>                   245                    250              255 | 768 |
| gaa tat act ccg ata cca gaa att aat cat caa tgg act aga cat tca<br>Glu Tyr Thr Pro Ile Pro Glu Ile Asn His Gln Trp Thr Arg His Ser<br>            260                    265                    270 | 816 |
| cca gag tat atg gag cga att gca aaa gta ccc cct ggc ggt tct ttg<br>Pro Glu Tyr Met Glu Arg Ile Ala Lys Val Pro Pro Gly Gly Ser Leu<br>                   275                    280                    285 | 864 |
| tat caa aaa tat gtt gat gcc ttt aag cgt caa tat cct ggt aag cca<br>Tyr Gln Lys Tyr Val Asp Ala Phe Lys Arg Gln Tyr Pro Gly Lys Pro<br>290                    295                    300 | 912 |
| agc atg act gtt aaa gaa aat cat ggc ggt act cat att cac cca tat<br>Ser Met Thr Val Lys Glu Asn His Gly Gly Thr His Ile His Pro Tyr<br>305                    310                    315              320 | 960 |
| tta aat agg gta att tca gct cgt gag atg gca aga tta caa aca ttt<br>Leu Asn Arg Val Ile Ser Ala Arg Glu Met Ala Arg Leu Gln Thr Phe<br>                   325                    330                    335 | 1008 |
| cct gat tca ttc att ttt gaa ggg aca atg aaa aaa gca atg tgg caa<br>Pro Asp Ser Phe Ile Phe Glu Gly Thr Met Lys Lys Ala Met Trp Gln<br>            340                    345                    350 | 1056 |
| att ggt aat gct gta ccg cca cgt tta gca gaa tgt atc ggc tat gca<br>Ile Gly Asn Ala Val Pro Pro Arg Leu Ala Glu Cys Ile Gly Tyr Ala<br>                   355                    360                    365 | 1104 |
| cta ata cct tat tta aat aag att gcg ctt aat act aag aat aaa gtt<br>Leu Ile Pro Tyr Leu Asn Lys Ile Ala Leu Asn Thr Lys Asn Lys Val<br>370                    375                    380 | 1152 |
| gat gtt act tgt att gat cag act gag tta gtg ttt gat taa<br>Asp Val Thr Cys Ile Asp Gln Thr Glu Leu Val Phe Asp<br>385                    390                    395 | 1194 |

<210> SEQ ID NO 2
<211> LENGTH: 397
<212> TYPE: PRT
<213> ORGANISM: Nostoc sp.

<400> SEQUENCE: 2

Met Gln Ser Thr Gln Leu Ser Phe Phe Pro Asp Glu Asp Glu Asn Lys
1               5                   10                  15

Ser Thr Lys Lys Gln Lys Lys Pro Lys Leu Gly Arg Tyr Glu Arg Ile
            20                  25                  30

Lys Arg Glu Leu Glu Asn Asn Asp Ile Asp Pro Tyr Lys Lys Phe Ile
        35                  40                  45

Asp Val Asp Thr Pro Leu Ile Ala Ala Ser Gln Tyr Asn Phe Val Asp
    50                  55                  60

Leu Phe Cys Gly Ala Gly Gly Ile Thr Gln Gly Leu Ile Gln Ala Gly
65                  70                  75                  80

Phe Gln Ala Leu Ala Ser Val Glu Thr Ser Ser Ile Ala Ser Ala Thr
                85                  90                  95

```
His Gln Arg Asn Phe Pro His Cys His His Phe Cys Gly Asp Ile Glu
            100                 105                 110

Gln Phe Ser Pro Lys Ile Trp Leu Lys Gln Ile Gly Ser Pro Glu Val
        115                 120                 125

Asn Leu Val Val Gly Pro Pro Cys Gln Gly Phe Ser Val Ala Gly
    130                 135                 140

Lys Arg Asp Pro Lys Asp Pro Arg Asn Arg Leu Phe Tyr Glu Phe Val
145                 150                 155                 160

Arg Val Val Ser Glu Ile Arg Pro Trp Tyr Val Val Met Glu Asn Val
                165                 170                 175

Pro Gly Ile Leu Thr Ile Gln Asn Gly Asn Val Lys Gln Ala Ile Ile
            180                 185                 190

Glu Ala Phe Glu Ser Ile Gly Tyr Pro Asn Ile Ser Val Ala Ile Leu
        195                 200                 205

Glu Ser Ala Asp Tyr Gly Ile Pro Gln Ile Arg Pro Arg Ala Ile Phe
    210                 215                 220

Ile Ala Asn Arg Phe Gly Met Pro Asn Pro Tyr Pro Lys Ala Gln Leu
225                 230                 235                 240

Ser Pro Glu Lys Tyr Lys Pro Ile Glu Ser Ala Ile Ser Asp Leu Pro
                245                 250                 255

Glu Tyr Thr Pro Ile Pro Glu Ile Asn His Gln Trp Thr Arg His Ser
            260                 265                 270

Pro Glu Tyr Met Glu Arg Ile Ala Lys Val Pro Pro Gly Gly Ser Leu
        275                 280                 285

Tyr Gln Lys Tyr Val Asp Ala Phe Lys Arg Gln Tyr Pro Gly Lys Pro
    290                 295                 300

Ser Met Thr Val Lys Glu Asn His Gly Gly Thr His Ile His Pro Tyr
305                 310                 315                 320

Leu Asn Arg Val Ile Ser Ala Arg Glu Met Ala Arg Leu Gln Thr Phe
                325                 330                 335

Pro Asp Ser Phe Ile Phe Glu Gly Thr Met Lys Lys Ala Met Trp Gln
            340                 345                 350

Ile Gly Asn Ala Val Pro Pro Arg Leu Ala Glu Cys Ile Gly Tyr Ala
        355                 360                 365

Leu Ile Pro Tyr Leu Asn Lys Ile Ala Leu Asn Thr Lys Asn Lys Val
    370                 375                 380

Asp Val Thr Cys Ile Asp Gln Thr Glu Leu Val Phe Asp
385                 390                 395

<210> SEQ ID NO 3
<211> LENGTH: 735
<212> TYPE: DNA
<213> ORGANISM: Nostoc sp.
<220> FEATURE:
<221> NAME/KEY: CDS
<222> LOCATION: (1)..(735)

<400> SEQUENCE: 3 gtg aat gaa gaa caa aat cta gta gag ata att cag cgc cag ttc aga     48
Met Asn Glu Glu Gln Asn Leu Val Glu Ile Ile Gln Arg Gln Phe Arg
  1               5                  10                  15 caa aac tca act caa cta caa gtc ttt aac ctc tta tca gat gaa aaa     96
Gln Asn Ser Thr Gln Leu Gln Val Phe Asn Leu Leu Ser Asp Glu Lys
             20                  25                  30 tgg cat tgt agg gaa tgt gaa ggt aag aaa ata ggc tca aat cag tac    144
Trp His Cys Arg Glu Cys Glu Gly Lys Lys Ile Gly Ser Asn Gln Tyr
         35                  40                  45
```

-continued

```
gct ggt ggt gga ggt att cag ggg tta caa cgt ggg aca agg agt cgt    192
Ala Gly Gly Gly Gly Ile Gln Gly Leu Gln Arg Gly Thr Arg Ser Arg
 50                  55                  60 cca ggt ctt gta att gaa acg acc aag aat tac tgt cca act tgt caa    240
Pro Gly Leu Val Ile Glu Thr Thr Lys Asn Tyr Cys Pro Thr Cys Gln
 65                  70                  75                  80 caa gta cgc tta gga gat caa tgg aca gga gag att aaa tca gct aat    288
Gln Val Arg Leu Gly Asp Gln Trp Thr Gly Glu Ile Lys Ser Ala Asn
                 85                  90                  95 tcc gca tca aat ata cca gcg tct tta gtt gag aga att tta caa gtt    336
Ser Ala Ser Asn Ile Pro Ala Ser Leu Val Glu Arg Ile Leu Gln Val
             100                 105                 110 tat tcc tat aca gat gta ata gaa caa aga cag aga gaa aaa cat gaa    384
Tyr Ser Tyr Thr Asp Val Ile Glu Gln Arg Gln Arg Glu Lys His Glu
         115                 120                 125 ttg gta att gat cat cga ttc ccg atg gaa cgt tgg gga gct agt gag    432
Leu Val Ile Asp His Arg Phe Pro Met Glu Arg Trp Gly Ala Ser Glu
     130                 135                 140 cct cca cac tta act tct atg agt gat gat gaa att aag caa aag ttt    480
Pro Pro His Leu Thr Ser Met Ser Asp Asp Glu Ile Lys Gln Lys Phe
145                 150                 155                 160 caa ttg tta aaa aaa gac gca tca ggt aat cac aat ctt tta aaa tcg    528
Gln Leu Leu Lys Lys Asp Ala Ser Gly Asn His Asn Leu Leu Lys Ser
                165                 170                 175 aga agt tgt gag cgc tgt atc aaa act ggt aaa aga ggt aca cct ata    576
Arg Ser Cys Glu Arg Cys Ile Lys Thr Gly Lys Arg Gly Thr Pro Ile
            180                 185                 190 ggc atc cat ttt tgg tat caa ggt gga gaa gat tgg cct tct cca cat    624
Gly Ile His Phe Trp Tyr Gln Gly Gly Glu Asp Trp Pro Ser Pro His
        195                 200                 205 caa cgt ggt gct gaa gca gaa gaa ggc tgt gtt gga tgt ggt tgg tat    672
Gln Arg Gly Ala Glu Ala Glu Glu Gly Cys Val Gly Cys Gly Trp Tyr
    210                 215                 220 aat ttt gaa gta tgg cgt aac gct att aat caa aca cta act cag tct    720
Asn Phe Glu Val Trp Arg Asn Ala Ile Asn Gln Thr Leu Thr Gln Ser
225                 230                 235                 240 gat caa tac aag taa                                                735
Asp Gln Tyr Lys
                245
```

<210> SEQ ID NO 4
<211> LENGTH: 244
<212> TYPE: PRT
<213> ORGANISM: Nostoc sp.

<400> SEQUENCE: 4

```
Met Asn Glu Glu Gln Asn Leu Val Glu Ile Ile Gln Arg Gln Phe Arg
 1               5                  10                  15

Gln Asn Ser Thr Gln Leu Gln Val Phe Asn Leu Leu Ser Asp Glu Lys
                 20                  25                  30

Trp His Cys Arg Glu Cys Glu Gly Lys Lys Ile Gly Ser Asn Gln Tyr
             35                  40                  45

Ala Gly Gly Gly Gly Ile Gln Gly Leu Gln Arg Gly Thr Arg Ser Arg
         50                  55                  60

Pro Gly Leu Val Ile Glu Thr Thr Lys Asn Tyr Cys Pro Thr Cys Gln
 65                  70                  75                  80

Gln Val Arg Leu Gly Asp Gln Trp Thr Gly Glu Ile Lys Ser Ala Asn
                 85                  90                  95
```

-continued

```
Ser Ala Ser Asn Ile Pro Ala Ser Leu Val Glu Arg Ile Leu Gln Val
                100                 105                 110

Tyr Ser Tyr Thr Asp Val Ile Glu Gln Arg Gln Arg Glu Lys His Glu
            115                 120                 125

Leu Val Ile Asp His Arg Phe Pro Met Glu Arg Trp Gly Ala Ser Glu
130                 135                 140

Pro Pro His Leu Thr Ser Met Ser Asp Asp Glu Ile Lys Gln Lys Phe
145                 150                 155                 160

Gln Leu Leu Lys Lys Asp Ala Ser Gly Asn His Asn Leu Leu Lys Ser
                165                 170                 175

Arg Ser Cys Glu Arg Cys Ile Lys Thr Gly Lys Arg Gly Thr Pro Ile
            180                 185                 190

Gly Ile His Phe Trp Tyr Gln Gly Gly Glu Asp Trp Pro Ser Pro His
        195                 200                 205

Gln Arg Gly Ala Glu Ala Glu Glu Gly Cys Val Gly Cys Gly Trp Tyr
    210                 215                 220

Asn Phe Glu Val Trp Arg Asn Ala Ile Asn Gln Thr Leu Thr Gln Ser
225                 230                 235                 240

Asp Gln Tyr Lys

<210> SEQ ID NO 5
<211> LENGTH: 27
<212> TYPE: DNA
<213> ORGANISM: Nostoc sp.

<400> SEQUENCE: 5
gtctttgttc tattacatct gtatagg                                        27

<210> SEQ ID NO 6
<211> LENGTH: 27
<212> TYPE: DNA
<213> ORGANISM: Nostoc sp.

<400> SEQUENCE: 6
catgaattgg taattgatca tcgattc                                        27

<210> SEQ ID NO 7
<211> LENGTH: 27
<212> TYPE: DNA
<213> ORGANISM: Nostoc sp.

<400> SEQUENCE: 7
aggttaaaga cttgtagttg agttgag                                        27

<210> SEQ ID NO 8
<211> LENGTH: 27
<212> TYPE: DNA
<213> ORGANISM: Nostoc sp.

<400> SEQUENCE: 8
aaaatggcat tgtagggaat gtgaagg                                        27

<210> SEQ ID NO 9
<211> LENGTH: 52
<212> TYPE: DNA
<213> ORGANISM: Nostoc sp.

<400> SEQUENCE: 9
gctggatccg gaggttaatt aaatgcaaag cacacaactt tctttttttc ct            52
```

```
<210> SEQ ID NO 10
<211> LENGTH: 42
<212> TYPE: DNA
<213> ORGANISM: Nostoc sp.

<400> SEQUENCE: 10
ctaggatcct taatcaaaca ctaactcagt ctgatcaata ca                          42

<210> SEQ ID NO 11
<211> LENGTH: 52
<212> TYPE: DNA
<213> ORGANISM: Nostoc sp.

<400> SEQUENCE: 11
acaggatccg gaggttaatt aagtgaatga agaacaaaat ctagtagaga ta              52

<210> SEQ ID NO 12
<211> LENGTH: 42
<212> TYPE: DNA
<213> ORGANISM: Nostoc sp.

<400> SEQUENCE: 12
attggatcct tacttgtatt gatcagactg agttagtgtt tg                          42
```